US011795438B2

(12) United States Patent
Kinooka et al.

(10) Patent No.: US 11,795,438 B2
(45) Date of Patent: *Oct. 24, 2023

(54) COMPOSITION FOR PROMOTING PROLIFERATION OF PLURIPOTENT STEM CELLS, AND METHOD FOR PROMOTING PROLIFERATION OF PLURIPOTENT STEM CELLS

(71) Applicant: Osaka University, Osaka (JP)

(72) Inventors: Masahiro Kinooka, Osaka (JP); Meehae Kim, Osaka (JP); Yukako Fujinaga, Osaka (JP)

(73) Assignee: Osaka University, Osaka (JP)

( * ) Notice: Subject to any disclaimer, the term of this patent is extended or adjusted under 35 U.S.C. 154(b) by 404 days.

This patent is subject to a terminal disclaimer.

(21) Appl. No.: 16/471,312

(22) PCT Filed: Dec. 19, 2017

(86) PCT No.: PCT/JP2017/045574
§ 371 (c)(1),
(2) Date: Jun. 19, 2019

(87) PCT Pub. No.: WO2018/117110
PCT Pub. Date: Jun. 28, 2018

(65) Prior Publication Data
US 2020/0017836 A1  Jan. 16, 2020

(30) Foreign Application Priority Data
Dec. 20, 2016 (JP) .................... 2016-247064

(51) Int. Cl.
*C12N 5/074* (2010.01)
(52) U.S. Cl.
CPC ...... *C12N 5/0696* (2013.01); *C12N 2501/998* (2013.01)
(58) Field of Classification Search
CPC .. C12N 5/0696; C12N 2501/998; C12N 5/10; C12N 5/0606
See application file for complete search history.

(56) References Cited

U.S. PATENT DOCUMENTS

| 2009/0155222 A1* | 6/2009 | Ward | C12N 15/1138 435/377 |
| 2012/0164729 A1 | 6/2012 | Tomizawa | |
| 2012/0220031 A1 | 8/2012 | Sekiguchi et al. | |
| 2015/0329831 A1 | 11/2015 | Kinooka et al. | |
| 2017/0130206 A1 | 5/2017 | Kinooka et al. | |
| 2018/0023057 A1* | 1/2018 | Sakai | C12N 5/0696 435/366 |

FOREIGN PATENT DOCUMENTS

| CN | 102597217 A | 7/2012 |
| CN | 105051185 A | 11/2015 |
| JP | 2014-143229 A | 8/2012 |
| WO | 2014/104207 A1 | 7/2014 |
| WO | 2015/199243 A1 | 12/2015 |
| WO | 2016/121840 A1 | 8/2016 |

OTHER PUBLICATIONS

Toh et al. "Modulation of integrin and E-cadherin-mediated adhesions to spatially control heterogeneity in human pluripotent stem cell differentiation." Biomaterials.May 2015;50:87-97. (Year: 2015).*
Mohamet et al. "Abrogation of E-Cadherin-Mediated Cellular Aggregation Allows Proliferation of Pluripotent Mouse Embryonic Stem Cells in Shake Flask Bioreactors." PLOS One Sep. 23, 2010;5(9):e12921. (Year: 2010).*
Extended European Search Report issued in corresponding European Patent Application No. 17884218.3 dated Oct. 10, 2019.
Kim et al., "A Simple and Robust Method for Culturing Human-Induced Pluripotent Stem Cells in an Undifferentiated State Using Botulinum Hemagglutinin," Biotechnology Journal, 13: 1700384 (2018).
Kim et al., "Maintenance of an undifferentiated state of human induced pluripotent stem cells through migration-dependent regulation of the balance between cell-cell and cell-substrate interactions," Journal of Bioscience and Bioengineering, 119: 617-622 (2015).
International Search Report issued in corresponding International Patent Application No. PCT/JP2017/045574 dated Feb. 6, 2018.
Office Action issued in corresponding Chinese Patent Application No. 201780078568.7 dated Apr. 29, 2023.
First Examination Report issued in corresponding Australian Patent Application No. 2017379330 dated Mar. 31, 2023.
Office Action issued in corresponding Chinese Patent Application No. 201780078568.7 dated Sep. 13, 2022.

* cited by examiner

*Primary Examiner* — Titilayo Moloye
(74) *Attorney, Agent, or Firm* — Morgan, Lewis & Bockius LLP

(57) ABSTRACT

Provided are a method for promoting the proliferation of pluripotent stem cells and a proliferation promoting composition used in the method. In one aspect, a composition for promoting the proliferation of pluripotent stem cells includes hemagglutinin or modified hemagglutinin. In another aspect, a method for promoting the proliferation of pluripotent stem cells includes culturing pluripotent stem cells in a culture medium to which the proliferation promoting composition of the present disclosure has been added.

5 Claims, 4 Drawing Sheets

COMPOSITION FOR PROMOTING PROLIFERATION OF PLURIPOTENT STEM CELLS, AND METHOD FOR PROMOTING PROLIFERATION OF PLURIPOTENT STEM CELLS

TECHNICAL FIELD

The present disclosure relates to a composition for promoting the proliferation of pluripotent stem cells and a method for promoting the proliferation of pluripotent stem cells.

BACKGROUND ART

In the stem cell industry, including regenerative medicine, pluripotent stem cells need to be cultured in large quantities while maintaining their undifferentiated state.

To proliferate pluripotent stem cells such as iPS cells while maintaining their undifferentiated state, Patent Document 1 discloses culturing pluripotent stem cells in the presence of activin.

On the other hand, Patent Documents 2 and 3 disclose a method for removing cells deviated from the undifferentiated state, which emerge during culture of pluripotent stem cells, by using hemagglutinin and modified hemagglutinin. Patent Document 3 discloses a method for dividing a cell aggregate into small aggregates in suspension culture of pluripotent stem cells by using hemagglutinin.

PRIOR ART DOCUMENTS

Patent Documents

Patent Document 1: JP 2012-143229 A
Patent Document 2: WO 2014/104207
Patent Document 3: WP 2015/199243

DISCLOSURE OF INVENTION

Problem to be Solved by the Invention

The present disclosure provides a composition for promoting the proliferation of pluripotent stem cells and a method for promoting the proliferation of pluripotent stem cells.

Means for Solving Problem

In one aspect, the present disclosure relates to a composition for promoting the proliferation of pluripotent stem cells. The composition contains hemagglutinin or modified hemagglutinin as an active ingredient.

In another aspect, the present disclosure relates to a method for promoting the proliferation of pluripotent stem cells. The method includes culturing pluripotent stem cells in a culture medium to which the proliferation promoting composition of the present disclosure has been added.

In yet another aspect, the present disclosure relates to a method for culturing pluripotent stem cells. The method includes performing the proliferation promoting method of the present disclosure.

Effects of the Invention

In one or more embodiments, the present disclosure has the effect of being able to promote the proliferation of pluripotent stem cells while maintaining their undifferentiated state.

DESCRIPTION OF THE INVENTION

Figure 1:
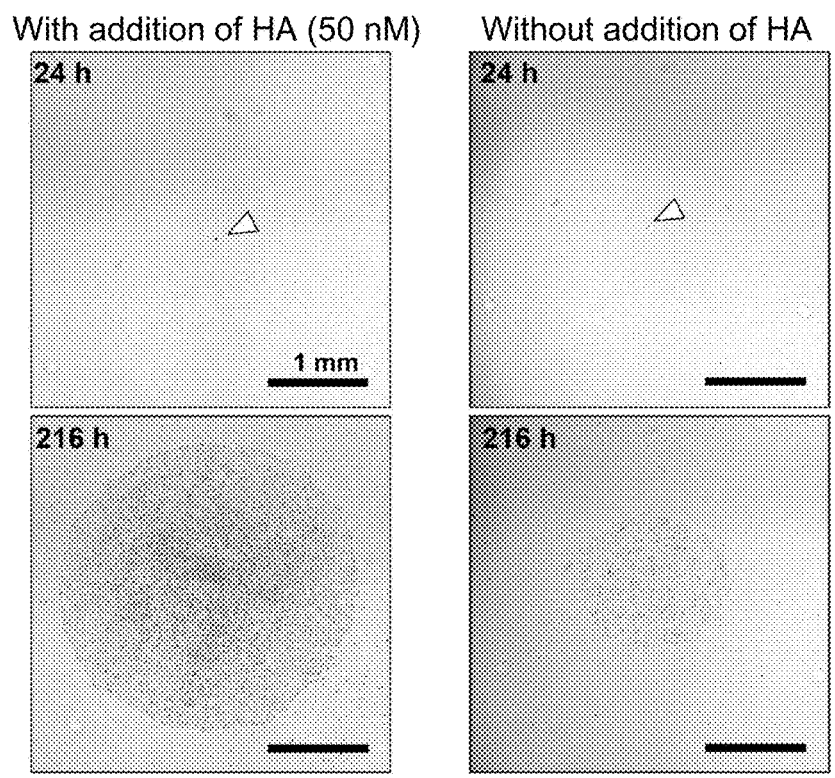
FIG. 1 shows the results of observing the proliferation promoting effect of hemagglutinin (HA) in clonal cell culture derived from single cells of human iPS cells.

The present inventors have been involved in the development of the technology of removing "cells deviated from the undifferentiated state" that emerge during culture of pluripotent stem cells. The "cells deviated from the undifferentiated state" tend to emerge in the central or peripheral portion of a colony of pluripotent stem cells during culture. It has been revealed that the "cells deviated from the undifferentiated state" that have emerged or emerge in the central portion of a colony can be removed by adding hemagglutinin to the colony during culture (WO 2014/104207 and WO 2015/199243). Moreover, it has also been revealed that when hemagglutinin is added to a cell aggregate formed in suspension culture of pluripotent stem cells, the cell aggregate can easily be divided into small aggregates (WO 2015/199243). These results may be attributed to the mechanism that hemagglutinin specifically binds to E-cadherin that is a cell adhesion molecule to inhibit cell-cell adhesion.

The present inventors conducted further intensive studies and found out that hemagglutinin has the effect of contributing to the promotion of proliferation of pluripotent stem cells. The present disclosure is based on the findings. Specifically, hemagglutinin is expected to function to reduce cell-cell adhesion so that the cell environment in the colonies or cell aggregates of pluripotent stem cells to be cultured may become more suitable for proliferation, thereby promoting the proliferation of pluripotent stem cells. Moreover, it is assumed that such a reduction in cell-cell adhesion will make the cell-cell adhesion strength uniform in the colonies of pluripotent stem cells to be cultured, and thus can suppress the emergence of "cells deviated from the undifferentiated state." However, the present disclosure should not be interpreted solely based on the above mechanism.

[Pluripotent Stem Cells]

In one or more non-limiting embodiments, pluripotent stem cells of the present disclosure are human pluripotent stem cells. In one or more non-limiting embodiments, the human pluripotent stem cells of the present disclosure are human iPS cells or human ES cells.

[Cells Deviated from Undifferentiated State]

In one or more non-limiting embodiments, the cells deviated from the undifferentiated state (i.e., deviated cells) of the present disclosure are different in morphology from cells in the undifferentiated state and therefore can be distinguished. Moreover, in one or more non-limiting embodiments, the emergence of deviated cells (cells in undifferentiated state have deviated from that state) can be confirmed by the disappearance of an undifferentiation marker. In one or more non-limiting embodiments, the undifferentiation marker is Oct3/4, Nanog, SSEA-4, or TEA-1-60.

[Hemagglutinin (HA)]

In one or more non-limiting embodiments, hemagglutinin of the present disclosure is hemagglutinin of *Clostridium botulinum*. Unless otherwise specified in the present disclosure, hemagglutinin is a neurotoxin complex (also referred to as a hemagglutinin complex). From the viewpoint of promoting the proliferation of cells having pluripotency, hemagglutinin may be a complex composed of two or three components selected from the group consisting of three hemagglutinin subcomponents HA1 (HA33), HA2 (HA17), and HA3 (HA70) of the neurotoxin complex of *Clostridium botulinum*, or a substance containing the complex. Moreover, hemagglutinin may be a complex composed of HA2 (HA17) and HA3 (HA70), a complex composed of the three components, or a substance containing the complex.

In one or more embodiments, from the viewpoint of promoting the proliferation of cells having pluripotency, the subcomponent HA3 (HA70) is preferably of *Clostridium botulinum* type A or *Clostridium botulinum* type B. In one or more non-limiting embodiments, the subcomponents HA1 (HA33) and HA2 (HA17) may be of any one of *Clostridium botulinum* type A, *Clostridium botulinum* type B, and *Clostridium botulinum* type C. In one or more non-limiting embodiments, each subcomponent of hemagglutinin may be of a recombinant type or a natural type.

[Modified Hemagglutinin]

In the present disclosure, hemagglutinin may be modified hemagglutinin as long as it has the effect of contributing to the promotion of proliferation of pluripotent stem cells. In one or more embodiments, the modified hemagglutinin may have at least one amino acid mutation in an amino acid sequence of one, two or three subcomponents. Examples of the modified hemagglutinin include those described in WO 2015/199243.

Unless otherwise specified in the present disclosure, the term "hemagglutinin" includes "modified hemagglutinin". Moreover, unless otherwise specified in the present disclosure, the "modified hemagglutinin" has the effect of contributing to the promotion of proliferation of pluripotent stem cells.

[Composition for Promoting Proliferation of Pluripotent Stem Cells]

In one aspect, the present disclosure relates to a composition for promoting the proliferation of pluripotent stem cells. The composition contains hemagglutinin or modified hemagglutinin.

From the viewpoint of promoting the proliferation of cells having pluripotency, the proliferation promoting composition of the present disclosure preferably contains an effective amount of hemagglutinin or modified hemagglutinin.

The proliferation promoting composition of the present disclosure can promote the proliferation of pluripotent stem cells. In one or more embodiments, the proliferation promoting composition of the present disclosure further allows the cells to be cultured with high uniformity. The term "high uniformity" may indicate, e.g., that the uniformity in cell-cell adhesion of cells to be cultured is high, that the uniformity in the cell-cell adhesion strength is high, or that cell aggregates are the same in size. The cell culture with high uniformity can contribute to the improvement in quality of the pluripotent stem cells obtained after proliferation. In one or more embodiments, unlike the conventional culture method, the proliferation promoting composition of the present disclosure allows the cells to be cultured with high uniformity between the cells in cell aggregates or cell colonies. Consequently, the number of cells that maintain the cell proliferative capacity is increased even at the position where the number of cells with low proliferative capacity has been increased in the conventional culture method, e.g., the position other than the inside of a cell aggregate or the peripheral portion of a cell colony. Thus, cells can be efficiently proliferated.

The proliferation promoting composition of the present disclosure may be added to a culture medium of pluripotent stem cells. In one or more embodiments, from the viewpoint of promoting the proliferation of cells having pluripotency, the concentration of the composition added to the culture medium may be determined so that the concentration of hemagglutinin or modified hemagglutinin in the culture medium after the addition of the composition is 5 nM or more, 10 nM or more, or 15 nM or more. From the same view point, the added concentration may be determined so that the concentration of hemagglutinin or modified hemagglutinin is 200 nM or less, 150 nM or less, or 100 nM or less.

The proliferation promoting composition of the present disclosure may be used in a method for promoting the proliferation of pluripotent stem cells and a method for culturing pluripotent stem cells, which will be described later.

[Method for Promoting Proliferation of Pluripotent Stem Cells]

In one aspect, the present disclosure relates to a method for promoting the proliferation of pluripotent stem cells. The method includes culturing pluripotent stem cells in a culture medium to which the proliferation promoting composition of the present disclosure has been added. The culture medium to which the proliferation promoting composition of the present disclosure is added is not particularly limited and may be a culture medium that can be used for culture of pluripotent stem cells. The added concentration of the proliferation promoting composition of the present disclosure may be the effective amount, as described above. In one or more embodiments, the added concentration may be determined so that the concentration of hemagglutinin or modified hemagglutinin in the culture medium after the addition of the composition is 5 nM or more, 10 nM or more, or 15 nM or more. From the same view point, the added concentration may be determined so that the concentration of hemagglutinin or modified hemagglutinin is 200 nM or less, 150 nM or less, or 100 nM or less.

Embodiment 1: Culture from Single Cell or Dispersed Cell

In one or more embodiments of the proliferation promoting method of the present disclosure, the present disclosure relates to a method for promoting the proliferation of pluripotent stem cells. The method includes seeding pluripotent stem cells in a single-cell state or a dispersed state, and culturing the pluripotent stem cells in a culture medium to which hemagglutinin or modified hemagglutinin has been added. In one or more embodiments, when the pluripotent stem cell population in the single-cell state or the dispersed state is brought into contact with hemagglutinin or modified hemagglutinin, the number of cells that maintain the cell proliferative capacity is increased even in the center of a colony during culture, so that the cells can be cultured with high uniformity. This can improve the efficiency of the promotion of cell proliferation, which in the end makes it possible to culture the cells at a high proliferation ratio, as compared to the conventional method.

Cells in the single-cell state of the present disclosure mean one or more cells obtained by dispersing a cell aggregate to a single-cell state with a cell dispersion treatment. The number of cells to be seeded is not particularly limited and may be either one or more than one cell. The method of the cell dispersion treatment is not particularly limited and may be, e.g., an enzyme treatment using trypsin, pronase, etc., a physical treatment such as pipetting, or a combination of these treatments.

Seeding cells in the dispersed state of the present disclosure means seeding a cell population that is obtained by the cell dispersion treatment of a cell aggregate, and that is in a state where not all cells are single cells. The cell population may include single cells.

The addition of hemagglutinin or modified hemagglutinin to the culture medium and the seeding of pluripotent stem cells may be performed in any desired order or simultaneously.

The proliferation promoting method of Embodiment 1 may be monolayer culture (adhesion culture) or suspension culture. For monolayer culture, it is preferable that hemagglutinin or modified hemagglutinin is added to the culture medium before a colony of pluripotent stem cells is formed.

Embodiment 2: Suspension Culture

In one or more embodiments of the proliferation promoting method of the present disclosure, the present disclosure relates to a method for promoting the proliferation of pluripotent stem cells. The method includes adding hemagglutinin or modified hemagglutinin to a culture medium for suspension culture of a cell aggregate of pluripotent stem cells, and culturing the pluripotent stem cells without dividing the cell aggregate into small aggregates. In one or more embodiments, the cell aggregate of the present disclosure means a spheroid cell cluster that is formed by suspension culture of pluripotent stem cells. In one or more embodiment, the phrase "without dividing the cell aggregate into small aggregates" of the present disclosure means that after hemagglutinin or modified hemagglutinin is added, no operation or treatment is performed to produce, e.g., a cell aggregate, a dispersed cell, and a single cell, which are smaller in size than the cell aggregate before the addition of hemagglutinin or modified hemagglutinin, until a part or the whole of the culture is completed.

In this embodiment, since the cells can be cultured with high uniformity, the proliferation of pluripotent stem cells can be promoted while reducing damage or stress to the cells. Consequently, the cells can be efficiently proliferated without dividing the cell aggregate.

Unless otherwise specified in the present disclosure, the phrase "dividing the cell aggregate into small aggregates" means dividing the cell aggregate of pluripotent stem cells due to hemagglutinin (see WO 2015/199243). WO 2015/199243 discloses that when hemagglutinin is added to a culture medium including cell aggregates of iPS cells during culture, the cell aggregates can be smoothly divided into small aggregates by, e.g., pipetting, although the cell clusters are composed of delicate cells such as iPS cells. This document also discloses that dividing the cell aggregate into small aggregates can improve the concentration of viable cells to be cultured.

On the other hand, in the proliferation promoting method of this embodiment (Embodiment 2), the cells are cultured without dividing the cell aggregate after hemagglutinin has acted on the cell aggregate. The mechanism of the proliferation promoting method of this embodiment can be assumed as follows. When hemagglutinin acts on the cell aggregate, the interaction between cells of the cell aggregate is reduced. Therefore, the number of cells that maintain the cell proliferative capacity is increased even inside the cell aggregate, so that the cells can be cultured with high uniformity. Consequently, larger cell aggregates can be formed, which in turn promotes efficient proliferation. However, the present disclosure should not be interpreted solely based on the above mechanism.

The proliferation promoting method of this embodiment (Embodiment 2) can promote the proliferation of cells while suppressing damage caused by the division of cell aggregates, even if the cells are delicate cells such as iPS cells.

In the present disclosure, the suspension culture of pluripotent stem cells may be performed by using, e.g., a bioreactor.

[Method for Culturing Pluripotent Stem Cells]

In another aspect, the present disclosure relates to a method for culturing pluripotent stem cells. The method includes performing the proliferation promoting method of the present disclosure. The proliferation promoting method of the present disclosure has already been described above.

The culture method of the present disclosure can promote the proliferation of pluripotent stem cells. In one or more embodiments, the culture method of the present disclosure further allows the cells to be cultured with high uniformity.

The present disclosure may also relate to the following embodiments.

[1] A composition for promoting proliferation of pluripotent stem cells, comprising:
hemagglutinin or modified hemagglutinin.

[2] A method for promoting proliferation of pluripotent stem cells, comprising: culturing pluripotent stem cells in a culture medium to which the composition according to [1] has been added.

[3] A method for promoting proliferation of pluripotent stem cells, comprising:
seeding pluripotent stem cells in a single-cell state or a dispersed state; and
culturing the pluripotent stem cells in a culture medium to which hemagglutinin or modified hemagglutinin has been added.

[4] The method according to [3], comprising:
adding hemagglutinin or modified hemagglutinin to the culture medium before a colony of the pluripotent stem cells is formed.

[5] A method for promoting proliferation of pluripotent stem cells, comprising: adding hemagglutinin or modified hemagglutinin to a culture medium for suspension culture of a cell aggregate of pluripotent stem cells; and culturing the pluripotent stem cells without dividing the cell aggregate into small aggregates.

[6] A method for culturing pluripotent stem cells; comprising:
performing the method according to any one of [2] to [5].

EXAMPLES

Hereinafter, the present disclosure will be described in more detail by way of examples. However, the following examples are merely illustrative and are not intended to limit the present disclosure.

[Adhesion Culture: Clonal Cell Culture]

The effect of hemagglutinin (HA) in clonal cell culture derived from single cells of human iPS cells was confirmed. The iPS cells (single cells) were seeded on an iMatrix-coated culture surface and cultured under the following conditions. Then, the effect of the presence or absence of HA was observed.

[Cells]
Human iPS cells: single cells of Tic strain
[Medium]
Stemfit (registered trademark) AK03 (manufactured by Ajinomoto Healthy Supply Co., Inc.)
[Vessel]
iMatrix-coated culture surface
[HA Preparing and Adding Method]
HA: Type B
Added concentration: 50 nM
Addition frequency (every day from the first day of culture)
[Culture Conditions]
5% $CO_2$ atmosphere at 37° C.
The HA complex was added to the culture medium from the start of culture (t=0).
[Observation]
At t=24 h and t=216 h, the cultured cells were observed with IN Cell Analyzer 2000 (trade name, manufactured by GE healthcare Bio-Sciences Corp.) and the images of the cultured cells were acquired. FIG. 1 shows the micrographs thus obtained.

[Results]
As shown in FIG. 1, the growth rate was higher in the culture using the culture medium that contained HA than in the culture using the culture medium that did not contain HA. The frequency of appearance of the cells deviated from the undifferentiated state was suppressed in the culture using the culture medium that contained HA, as compared to the culture using the culture medium that did not contain HA.

[Suspension Culture: Cell Aggregate Culture]

The effect of hemagglutinin (HA) on suspension culture of iPS cells was confirmed.

Figure 2:
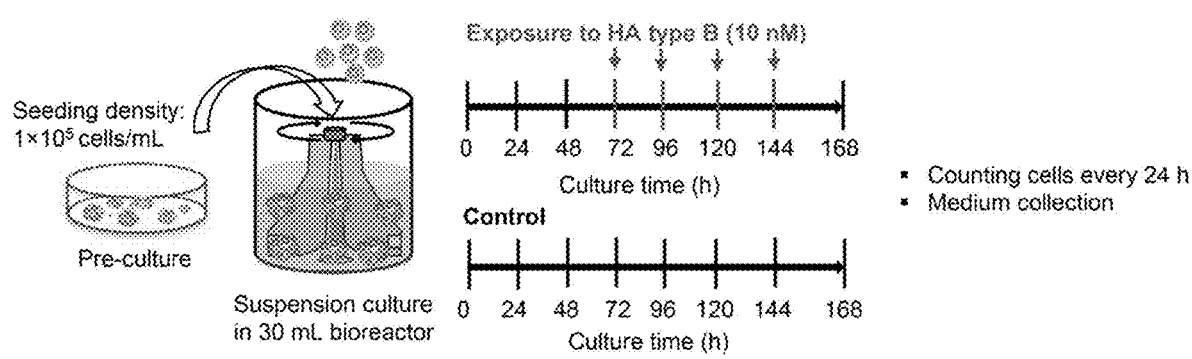
FIG. 2 is a schematic view of the experimental scheme in Examples.
Figure 3:
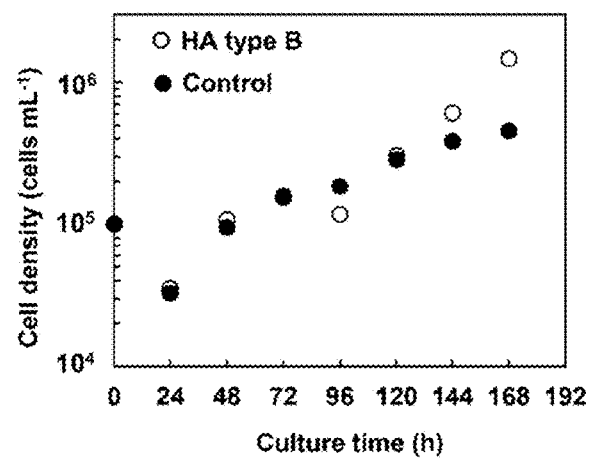
FIG. 3 is a diagram plotting the culture time and the cell density in suspension culture of cell aggregates of human iPS cells.
Figure 4:
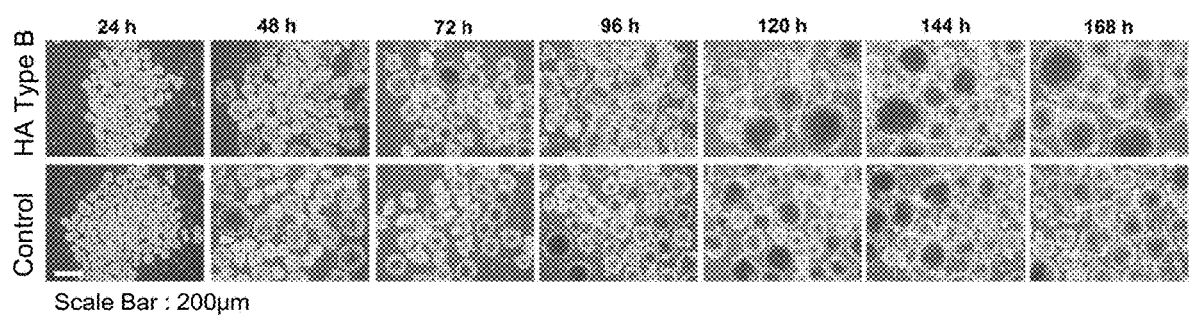
FIG. 4 shows the results of the micrographs of the effect of hemagglutinin (HA) in suspension culture of cell aggregates of human iPS cells.

[Cells]
Human iPS cells: single cells of Tic strain
[Medium]
mTeSR1 (STEMCELL Technologies)
[Vessel]
30 ml bioreactor (Able Co., Ltd.)
[Seeding Density]
$1.0 \times 10^5$ cells/mL
[HA Preparing and Adding Method]
HA: Type B
Added concentration: 10 nM
[Culture Conditions]
5% $CO_2$ atmosphere at 37° C.
The HA complex was added 72 hours after the start of culture (t=0) every 24 hours for 3 days so that the hemagglutinin concentration was 10 nM (FIG. 2).
[Observation]
The cultured cells were observed every 24 hours from t=0 with IN Cell Analyzer 2000 (trade name, manufactured by GE healthcare Bio-Sciences Corp.) and the images of the cultured cells were acquired, and further the cell density per volume of the culture medium was measured (FIGS. 3 and 4).

[Results]
The culture time was divided into 2 phases: the first phase from t=0 to t=72 h and the second phase from t=72 h to t=168 h. Then, the cell survival ratio ($\alpha$) and the apparent specific growth rate ($\mu$) in each phase were calculated (Table 1). As shown in Table 1, the proliferation speed was higher in the second phase to which HA was added than in the first phase and the second phase to which HA was not added. The size of the cell aggregates was uniform and the frequency of appearance of the cells deviated from the undifferentiated state was suppressed in the second phase to which HA was added, as compared to the first phase and the second phase to which HA was not added.

Method of calculation of $\alpha$ value and $\mu$ value $\alpha = X_{24}/X_0$ $X_0$=Cell density at seeding (0 h)
$X_{24}$=Cell density 24 hours after seeding $\mu = LN(X_2/X_1)/(t_2-t_1)$ $t_1$=24 h (first phase) or 96 h (second phase)
$t_2$=72 h (first phase) or 168 h (second phase)

TABLE 1

Comparison of cell survival ratio ($\alpha$) and apparent specific growth rate ($\mu$)

| | HA (Type B, 10 nM) | | Control | |
|---|---|---|---|---|
| | $1^{st}$ phase | $2^{nd}$ phase | $1^{st}$ phase | $2^{nd}$ phase |
| $\alpha$ (—) | 0.35 | | 0.33 | |
| $\mu$ ($h^{-1}$) | 0.031 | 0.035 | 0.033 | 0.013 |

[Suspension Culture: Cell Aggregate Culture 2]

As the effects of the addition of HA for proliferation of human iPS cell aggregates, two points were evaluated: the cell proliferation properties and the localization of cell division in the cell aggregates.

[Cell]
Human iPS cells: single cells of Tic strain
[Medium]
Stemfit (registered trademark) AK02 (manufactured by Ajinomoto Healthy
Supply Co., Inc.)
Frequency of replacement of medium: every 24 hours
[Vessel]
96 well plate V-bottom (manufactured by Sumitomo Bakelite Co., Ltd., PrimeSurface (registered trademark))
[HA Preparing and Adding Method]
HA: Type B
Added concentration (after culture for 24 hours): 0, 5, 10 nM
[Culture Conditions]
5% $CO_2$ atmosphere at 37° C.
Number of cells seeded: $3.0 \times 10^3$ cells/well
Culture time: 240 hours
[Measurement Items]
Cell proliferation properties: The number of cells in a cell aggregate and the apparent specific growth rate ($\mu$) in culture between 24 h and 168 h were measured.
Properties in cell aggregates: The localization of cell division was observed by fluorescent staining (nuclei=DAPI, divisible cells=anti-ki-67 antibody) of frozen sections.

Frequency of measurement: every 48 hours after culture for 24 hours

[Results of Cell Proliferation Properties]

The Tic strain was cultured in the culture media containing HA at a concentration of 0, 5, 10 nM under the above culture conditions. The number of cells in each cell aggregate and the specific growth rate ($\mu$) were measured as the proliferation properties.

Figure 5:
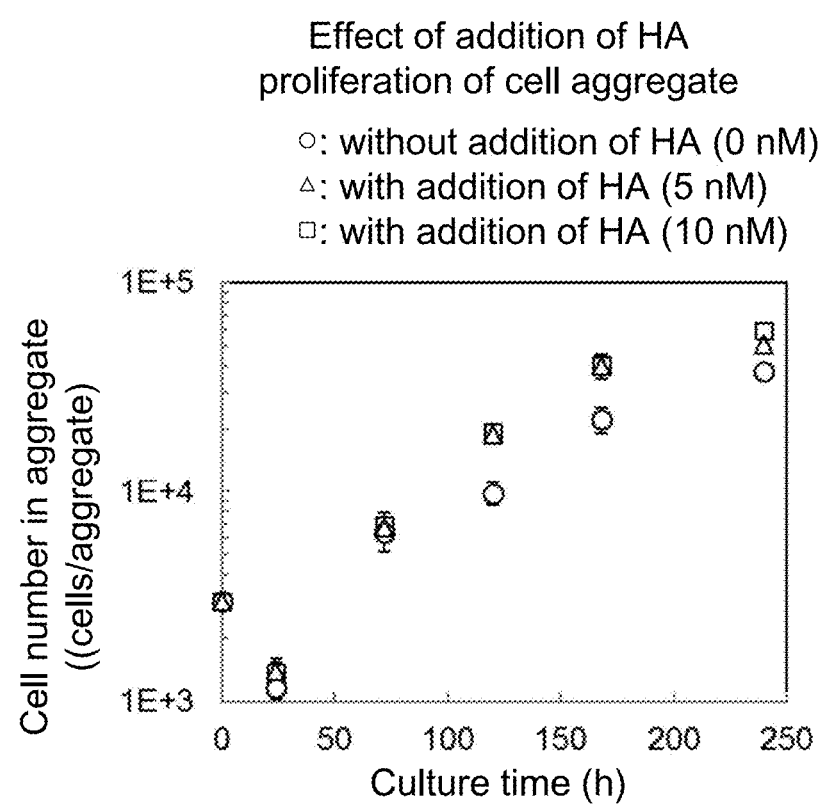
FIG. 5 shows an example of a graph that confirmed the effect of the addition of HA on the number of cells in a cell aggregate (○: without the addition of HA, Δ: with the addition of HA (5 nM), □: with the addition of HA (10 nM)).

FIG. 5 shows the results of the number of cells in a cell aggregate. As shown in FIG. 5, the results confirmed that the number of cells in a cell aggregate was increased by the addition of HA (added concentration: Δ=5 nM, □=10 nM), as compared to without the addition of HA (○=0 nM). The specific growth rate ($\mu$) was calculated based on the following formulas as an apparent specific growth rate in culture between 24 h and 168 h. Table 2 shows the results. As shown in Table 2, the results confirmed that the specific growth rate ($\mu$) was higher with the addition of HA than without the addition of HA, and that the cell proliferation was promoted.

$$\mu = LN(X_2/X_1)/(t_2-t_1)$$

$X_1=t_1=24$ h
$X_2=t_2=168$ h

TABLE 2

Comparison of proliferation properties

| HA concentration (nM) | $\mu$ ($10^{-2}h^{-1}$) |
|---|---|
| 0 | 2.04 ± 0.12 |
| 5 | 2.33 ± 0.15 |
| 10 | 2.35 ± 0.05 |

[Results of Properties in Cell Aggregates]

Figure 6:
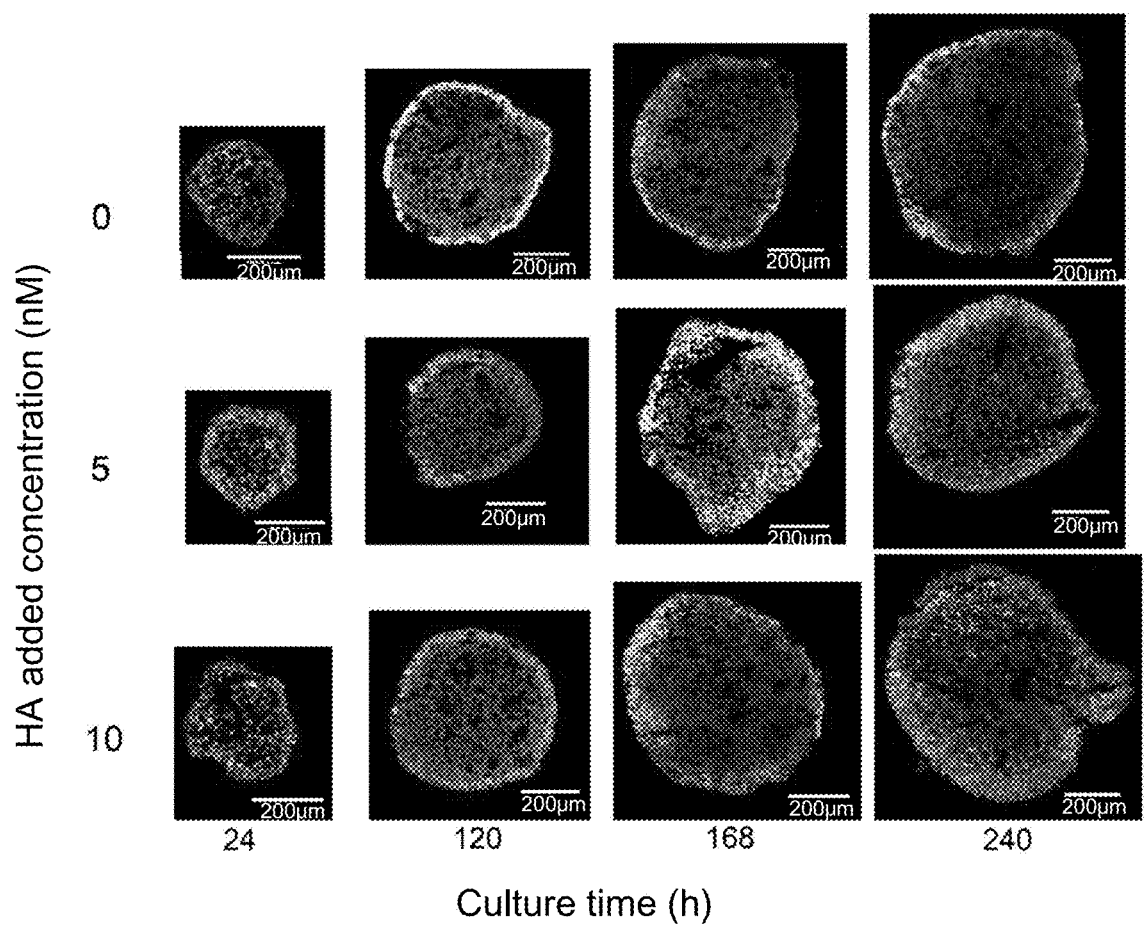
FIG. 6 shows an example of the results of the micrographs of fluorescent staining of the localization of divisible cells in cell aggregates.

The properties in cell aggregates were observed by fluorescent staining with a microscope. The nuclei were stained with DAPI (red) and the divisible cells were stained with the anti-ki-67 antibody (green) so that the localization of the divisible cells in the cell aggregates was confirmed. FIG. 6 shows an example of the results.

When HA was not added, the divisible cells (ki-67 positive cells) were substantially uniformly present (i.e., portions represented by yellow) in a cell aggregate after 24 hours of culture. Then, no divisible cell was observed inside the cell aggregate and the cells were localized only in the peripheral portion. In other words, the cells divided only in the peripheral portion of the cell aggregate, and thus the number of cells in the cell aggregate was increased.

When HA was added (5, 10 nM), the cells had the same tendency as those without the addition of HA after 24 hours of culture. However, in the subsequent culture, the frequency of the divisible cells was increased in the peripheral portion of the aggregate, as compared to without the addition of HA. In the culture with the addition of HA at 10 nM, the divisible cells were also present inside the cell aggregate. Thus, it was evident that the addition of HA improved the frequency of cell division in cell aggregates and increased the growth rate. Moreover, it was confirmed that the increase in growth rate due to HA indicated the HA concentration dependence.

INDUSTRIAL APPLICABILITY

The method and composition of the present disclosure are useful, e.g., in the field of regenerative medicine.

The invention claimed is:

1. A method for promoting proliferation of pluripotent stem cells, comprising:
   (i) seeding pluripotent stem cells in a single-cell state or a dispersed state;
   (ii) adding hemagglutinin or modified hemagglutinin to a culture medium before a colony of the pluripotent stem cells is formed;
   (iii) culturing the pluripotent stem cells until a colony of pluripotent stem cells informed; and
   (iv) culturing the colony of pluripotent stem cells in an adhesion culture for 72 hours or more in a culture medium in which hemagglutinin or modified hemagglutinin has been added to the culture medium once every twenty-four hours.

2. The method according to claim 1, further comprising suppressing a frequency of appearance of cells deviated from undifferentiated state.

3. The method according to claim 1, wherein the concentration of hemagglutinin or modified hemagglutinin in the culture medium in (ii) and (iv) is 50 nM or less.

4. The method according to claim 1, wherein the hemagglutinin is hemagglutinin of Clostridium botulinum.

5. The method according to claim 1, wherein the hemagglutinin is a complex composed of HA2 (HA17) and HA3 (HA70) or a complex composed of HA1 (HA33), HA2 (HA17) and HA3 (HA70).

* * * * *